(12) United States Patent
Fernández Rodríguez et al.

(10) Patent No.: US 8,962,602 B2
(45) Date of Patent: Feb. 24, 2015

(54) ANTICANCER STEROIDAL LACTONES UNSATURATED IN POSITION 7 (8)

(75) Inventors: Rogelio Fernández Rodríguez, Madrid (ES); José Fernando Reyes Benítez, Madrid (ES); Andrés Francesch Solloso, Madrid (ES); María del Carmen Cuevas Marchante, Madrid (ES)

(73) Assignee: Pharma Mar, S.A., Madrid (ES)

( * ) Notice: Subject to any disclaimer, the term of this patent is extended or adjusted under 35 U.S.C. 154(b) by 0 days.

(21) Appl. No.: 13/642,910

(22) PCT Filed: Apr. 26, 2011

(86) PCT No.: PCT/EP2011/056566
§ 371 (c)(1),
(2), (4) Date: Oct. 23, 2012

(87) PCT Pub. No.: WO2011/134954
PCT Pub. Date: Nov. 3, 2011

(65) Prior Publication Data
US 2013/0040921 A1    Feb. 14, 2013

(30) Foreign Application Priority Data
Apr. 27, 2010   (EP) .................................. 10382095

(51) Int. Cl.
*A61K 31/585*   (2006.01)
*C07J 19/00*    (2006.01)
*C07J 71/00*    (2006.01)

(52) U.S. Cl.
CPC ............... *C07J 19/00* (2013.01); *C07J 71/001* (2013.01)
USPC ........................................................ 514/175

(58) Field of Classification Search
None
See application file for complete search history.

(56) References Cited

U.S. PATENT DOCUMENTS

2009/0018088 A1   1/2009   Valdes et al.

FOREIGN PATENT DOCUMENTS

| CA | 2418458 | 8/2004 |
| CN | 1793132 | 6/2006 |
| JP | 4 290899 | 10/1992 |
| WF | WO 2006/120472 | 11/2006 |
| WO | WO 00/47215 | 8/2000 |
| WO | WO 01/79256 | 10/2001 |
| WO | WO 2007/130124 | 11/2007 |

OTHER PUBLICATIONS

Laphookhieo et al., "Cytotoxic Cardenolide Glycoside from the Seeds of *Cerbera odollam*," Phytochemistry, 65, pp. 507-510, 2004.

Li et al., "Cytotoxic Cardenolides from the stems of *Periploca forrestii*," Steroids, 77, pp. 375-381, 2012.

Zhao et al., "Bioactive Cardenolides from the Stems and Twigs of *Nerium oleander*," J. Natl. Prod., 70, pp. 1098-1103, 2007.

Boyd, M. R. et al. "Some practical considerations and applications of the National Cancer Institute in vitro Anticancer Drug Discovery Design" *Drug Dev. Res.* 1995, 34, 91-109.

Cheenpracha, S. et al. "New Cytotoxic Cardenolide Glycoside from the Seeds of *Cerbera manghas*" *Chem. Pharm. Bull.* 2004, 52, 1023-1025.

Faircloth, G. T. et al. "A simple screening procedure for the quantitative measurement of cytotoxicity to resting primary lymphocyte cultures" *Jounrnal of Tissue Culture Methods*, 1988, 11, 201-205.

Gao, H. et al. "Bafadienolides and their antitumor activity" *Nat. Prod. Rep.* 2011, 28, 953-969.

Guiqin Qu, M. Y. et al. "Novel cytotoxic bafadienolides derived from bufalin by microbial hydroxylation and their structure-activity relationships" *J. Steroid Biochem. Mol. Biol.* 2004, 91, 87-98.

Jian Han, M. Y. et al. "Microbial Hydroxylation of Bufalin by *Cunninghamella blakesleana* and *Mucor spinosus*" *J. Nat. Prod.* 2005, 68, 626-628.

Jing, Y. et al. "Selective Inhibitory Effect of Bufalin on Growth of Human Tumor Cells in vitro: Association with the Induction of Apoptosis in Leukemia HL-60 Cells" *Jpn. J. Cancer Res.* 1994, 85, 645-651.

Kamano, Y. et al. "QSAR Evaluation of the Ch'an Su and Related Bufadienolides against the Colchicine-Resistance Primary Liver Carcinoma Cell Line PLC/PRF/5$^1$," *J. Med. Chem.* 2002, 45, 5440-5447.

Kamano, Y. et al. "Rhinovirus Inhibition by Bufadienolides" *Chem. Pharm. Bull.* 1988, 36, 326-332.

Kamano, Y. et al. "Structure-Cytotoxicity Activity Relationship for the Toad Poison Bafadienolides" *Bioorg. Med. Chem.* 1998, 6, 1103-1115.

(Continued)

*Primary Examiner* — Craig Ricci
(74) *Attorney, Agent, or Firm* — Kenneth H. Sonnenfeld; King & Spalding LLP

(57) ABSTRACT

A compound of general formula (I), wherein $R_1$-$R_{17}$ and the ------ line take various meanings for use in the treatment of cancer.

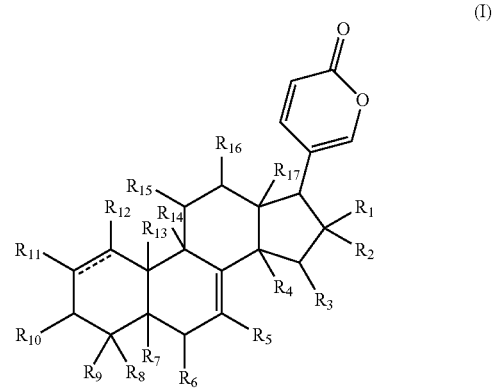

(I)

27 Claims, No Drawings

(56) References Cited

OTHER PUBLICATIONS

Kopp, B. et al. "Bufadienolides from *Urginea maritima* from Egypt" *Phytochemistry* 1996, 42, 513-522.

Krenn, L. et al. "Bufadienolides from animal and plant sources" *Phytochemistry* 1998, 48, 1-29.

Kupchan, S. M. et al. "Tumor Inhibitors. LXV. Bersenogenin, Berscillogenin, and 3-Epiberscillogenin, Three New Cytotoxic Bufadienolides from *Bersama abyssinica*" *J. Org. Chem.* 1971, 18, 2611-2616.

Kupchan, S. M. et al. "Tumor Inhibitors. LXV. Isolation and Structural Elucidation of Novel Bufadienolides, the Cytotoxic Principles of *Bersama abyssinica*" *Bioorg. Chem.* 1971, 1, 13-31.

Majinda, R. R. T. et al. "Bufadienolides and Other Constituents of *Urginea sanguinea*" *Planta Med.* 1997, 63, 188-190.

Mosmann, T. "Rapid Colorimetric Assay for Cellular Growth and Survival: Application to Proliferation and Citotoxicity Assays" *Journal of Immunological Methods* 1983, 65, 55-63.

Nogawa, T. et al. "Isolation and Structure of Five New Cancer Cell Growth Inhibitory Bufadienolides from the Chinese Traditional Drug Ch'an Su" *J. Nat. Prod.* 2001, 64, 1148-1152.

Skehan, P. et al. "New Colorimetric Cytotoxicity Assay for Anticancer-Drug Screening" *J. Ntl. Cancer Inst.* 1990, 82, 1107-1112.

Steyn, P. S. et al. "Bufadienolides of plant and animal origin" *Nat. Prod. Rep.* 1998, 15, 397-413.

Takechi, M. et al. "Structure-Activity relationships of synthetic cardiac glycosides" *Phytochemistry* 1996, 41, 125-127.

Verbiscar, A. J. et al. "Scilliroside and Other Scilla Compounds in Red Squill" *J. Agric. Foof. Chem.* 1988, 34, 973-979.

ANTICANCER STEROIDAL LACTONES UNSATURATED IN POSITION 7 (8)

FIELD OF THE INVENTION

The present invention relates to new anticancer compounds, pharmaceutical compositions containing them, and their use as anticancer agents.

BACKGROUND OF THE INVENTION

The present invention relates to compounds with some structural similarities to bufadienolide compounds disclosed in the prior art. For a review of bufadienolides see Huimin Gao et al in Nat. Prod. Rep., 2011, 28, 953.

The bufadienolide compounds reported in the prior art are natural steroids, originally isolated from terrestrial natural sources such as plants of the families Crassulaceae, Hyacinthaceae, Iridaceae, Melianthaceae, Ranunculaceae, and Santalaceaethe, and animals of the genus *Bufo* (toads), *Photinus* (fireflies), and *Rhabdophis* (snakes) (Steyn et al. Nat. Prod. Rep. 1998, 15, 397-413; Krenn et al. Phytochemistry, 1998, 48(1), 1-29).

Among these bufadienolide compounds, Scilliroside and other Scilla compounds have been isolated from the red squill, *Urginea maritima*, and are disclosed to be highly toxic, specially Scilliroside which affects the cardiovascular and central nervous systems, causing convulsions and death (Verbiscar et al. J. Agric. Food Chem. 1986, 34, 973-979; Kopp et al. Phytochemistry, 1996, 42(2), 513-522). Majinda et al. also isolated bufadienolide compounds from *Urginea sanguinea*, which make the plant unsafe to be used as a medicinal plant (Planta Med. 1997, 63, 188-190).

The antiviral activity against a series of rhinoviruses and the anti-herpetic activity of several bufadienolide compounds were evaluated by Kamano et al. (Chem. Pharm. Bull. 1988, 36(1), 326-332) and Takechi et al. (Phytochemistry, 1996, 41(1), 125-127), respectively, and they found that most of the compounds displayed some inhibitory activity.

Additionally, the cytotoxic activity of several bufadienolide compounds has been evaluated by several authors. Specifically, Jing et al. reported that bufalin has a potent growth-inhibitory effect on human cancer cells of leukaemia (HL-60, ML1, U937, and K562 cell lines), epithelioid carcinoma (HeLa cell line), hepatoma (PLC/PRF/5 cell line), and epidermoid carcinoma (A431 cell line), but it is less potent on mouse leukaemia M1, melanoma B16, and lymphoid neoplasm P388 cell lines and rat hepatoma AH66 and chromaffin cell PC12 cell lines. They also found that bufalin induces typical apoptosis in human leukaemia HL-60 cell line but not in human leukocytes (Jpn. J. Cancer Res. 1994, 85(6), 645-651).

Kupchan et al. disclosed several bufadienolide compounds isolated from *Bersama abyssinica* which showed inhibitory activity against human carcinoma of the nasopharynx (KB) cell line (Bioorg. Chem. 1971, 1, 13-31; J. Org. Chem. 1971, 36(18), 2611-2616).

Kamano et al. evaluated the cytotoxic activity of 80 bufadienolide and cardenolide compounds, isolated from the Chinese drug Ch'an Su (obtained from the skin glands of toads such as *Bufo gargarizans*), against a primary liver carcinoma PLC/PRF/5 cell line and the colchicine-resistant cell line of PLC/PRF/5. Of them, 16 were shown to have potent cytotoxicities ($IC_{50} < 10^{-3}$ µg/mL) against PLC/PRF/5 cell line (Bioorg. Med. Chem. 1998, 6, 1103-1115; J. Med. Chem. 2002, 45, 5440-5447). Additional bufadienolide compounds were isolated by Nogawa et al. from the same source, which were tested against human carcinoma of the nasopharyx (KB), human leukaemia (HL-60), murine leukaemia (MH60), pancreas adenocarcinoma (BXPC3), breast adenocarcinoma (MCF7), CNS glioblastoma (SF268), lung NSC (NCIH460), colon carcinoma (KM20L2), and prostate cancer (DU145) cell lines (J. Nat. Prod. 2001, 64, 1148-1152).

Ye et al. prepared novel bufadienolide compounds from bufalin by microbial hydroxylation. The compounds were tested against human hepatoma Bel-7402, human gastric cancer BGC-823, human cervical carcinoma HeLa, and human leukaemia HL-60 cell lines, showing some of them potent cytotoxicities comparable to that of bufalin (J. Steroid. Biochem. Mol. Biol. 2004, 91, 87-98; J. Nat. Prod. 2005, 68, 626-628).

Since cancer is a leading cause of death in animals and humans, several efforts have been and are still being undertaken in order to obtain an anticancer therapy active and safe to be administered to patients suffering from a cancer. The problem to be solved by the present invention is to provide compounds that are useful in the treatment of cancer.

SUMMARY OF THE INVENTION

In one aspect, the present invention is directed to compounds of general formula I or pharmaceutically acceptable salts, prodrugs or stereoisomers thereof

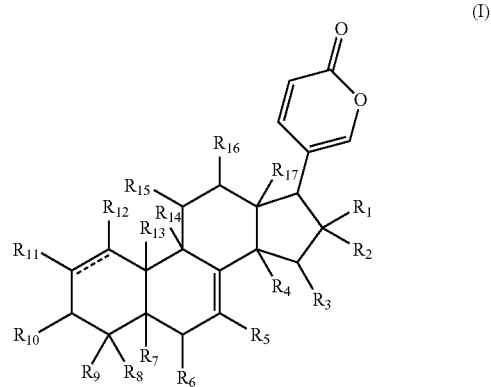

(I)

wherein each $R_1$ and $R_2$ is independently selected from hydrogen, halogen, $OR_a$, $OCOR_a$, and $OCOOR_a$, or $R_1$ and $R_2$ together are =O;

each $R_3$, $R_{15}$, and $R_{16}$ is independently selected from hydrogen, $OR_a$, $OCOR_a$, $OCOOR_a$, and =O, with the proviso that when a =O group exists the hydrogen of the C atom to which the =O is attached is absent;

each $R_4$, $R_5$, $R_6$, $R_7$, $R_{11}$, $R_{12}$, and $R_{14}$ is independently selected from hydrogen, $OR_a$, $OCOR_a$, and $OCOOR_a$;

each $R_8$, $R_9$, and $R_{17}$ is independently selected from hydrogen, $OR_a$, $OCOR_a$, $OCOOR_a$, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R_{10}$ is selected from hydrogen, $OR_b$, $OCOR_a$, $OCOOR_a$, and =O, with the proviso that when a =O group exists the hydrogen of the C atom to which the =O is attached is absent;

$R_{13}$ is selected from hydrogen, $COR_a$, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

each $R_a$ is independently selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group;

each $R_b$ is independently selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, substituted or unsubstituted heterocyclic group, and substituted or unsubstituted sugar; and the - - - - - - - line represents an additional bond, an epoxy group, or is absent.

In another aspect, the present invention is directed to a compound of formula I, or a pharmaceutically acceptable salt, prodrug or stereoisomer thereof, for use as a medicament, in particular as a medicament for treating cancer.

In a further aspect, the present invention is also directed to the use of a compound of formula I, or a pharmaceutically acceptable salt, prodrug or stereoisomer thereof, in the treatment of cancer, or in the preparation of a medicament, preferably for the treatment of cancer. Other aspects of the invention are methods of treatment, and compounds for use in these methods. Therefore, the present invention further provides a method of treating any mammal, notably a human, affected by cancer which comprises administering to the affected individual a therapeutically effective amount of a compound as defined above.

In a yet further aspect, the present invention is also directed to a compound of formula I, or a pharmaceutically acceptable salt, prodrug or stereoisomer thereof, for use as an anticancer agent.

In another aspect, the present invention is directed to pharmaceutical compositions comprising a compound of formula I, or a pharmaceutically acceptable salt, prodrug or stereoisomer thereof, together with a pharmaceutically acceptable carrier or diluent.

DETAILED DESCRIPTION OF THE INVENTION

The present invention relates to compounds of general formula I as defined above.

In these compounds the groups can be selected in accordance with the following guidance:

Alkyl groups may be branched or unbranched, and preferably have from 1 to about 12 carbon atoms. One more preferred class of alkyl groups has from 1 to about 6 carbon atoms. Even more preferred are alkyl groups having 1, 2, 3 or 4 carbon atoms. Methyl, ethyl, n-propyl, isopropyl and butyl, including n-butyl, tert-butyl, sec-butyl and isobutyl are particularly preferred alkyl groups in the compounds of the present invention. As used herein, the term alkyl, unless otherwise stated, refers to both cyclic and noncyclic groups, although cyclic groups will comprise at least three carbon ring members.

Preferred alkenyl and alkynyl groups in the compounds of the present invention may be branched or unbranched, have one or more unsaturated linkages and from 2 to about 12 carbon atoms. One more preferred class of alkenyl and alkynyl groups has from 2 to about 6 carbon atoms. Even more preferred are alkenyl and alkynyl groups having 2, 3 or 4 carbon atoms. The terms alkenyl and alkynyl as used herein refer to both cyclic and noncyclic groups, although cyclic groups will comprise at least three carbon ring members.

Suitable aryl groups in the compounds of the present invention include single and multiple ring compounds, including multiple ring compounds that contain separate and/or fused aryl groups. Typical aryl groups contain from 1 to 3 separated or fused rings and from 6 to about 18 carbon ring atoms. Preferably aryl groups contain from 6 to about 10 carbon ring atoms. Specially preferred aryl groups include substituted or unsubstituted phenyl, substituted or unsubstituted naphthyl, substituted or unsubstituted biphenyl, substituted or unsubstituted phenanthryl, and substituted or unsubstituted anthryl.

Suitable heterocyclic groups include heteroaromatic and heteroalicyclic groups containing from 1 to 3 separated and/or fused rings and from 5 to about 18 ring atoms. Preferably heteroaromatic and heteroalicyclic groups contain from 5 to about 10 ring atoms. Suitable heteroaromatic groups in the compounds of the present invention contain one, two or three heteroatoms selected from N, O or S atoms and include, e.g., coumarinyl including 8-coumarinyl, quinolyl including 8-quinolyl, isoquinolyl, pyridyl, pyrazinyl, pyrazolyl, pyrimidinyl, furyl, pyrrolyl, thienyl, thiazolyl, isothiazolyl, triazolyl, tetrazolyl, isoxazolyl, oxazolyl, imidazolyl, indolyl, isoindolyl, indazolyl, indolizinyl, phthalazinyl, pteridinyl, purinyl, oxadiazolyl, thiadiazolyl, furazanyl, pyridazinyl, triazinyl, cinnolinyl, benzimidazolyl, benzofuranyl, benzofurazanyl, benzothienyl, benzothiazolyl, benzoxazolyl, quinazolinyl, quinoxalinyl, naphthyridinyl and furopyridyl. Suitable heteroalicyclic groups in the compounds of the present invention contain one, two or three heteroatoms selected from N, O or S atoms and include, e.g., pyrrolidinyl, tetrahydrofuryl, dihydrofuryl, tetrahydrothienyl, tetrahydrothiopyranyl, piperidyl, morpholinyl, thiomorpholinyl, thioxanyl, piperazinyl, azetidinyl, oxetanyl, thietanyl, homopiperidyl, oxepanyl, thiepanyl, oxazepinyl, diazepinyl, thiazepinyl, 1,2,3,6-tetrahydropyridyl, 2-pyrrolinyl, 3-pyrrolinyl, indolinyl, 2H-pyranyl, 4H-pyranyl, dioxanyl, dioxanyl, 1,3-dioxolanyl, pyrazolinyl, dithianyl, dithiolanyl, dihydropyranyl, dihydrothienyl, pyrazolidinyl, imidazolinyl, imidazolidinyl, 3-azabicyclo[3.1.0]hexyl, 3-azabicyclo[4.1.0]heptyl, 3H-indolyl, and quinolizinyl.

The term sugar includes monosaccharides, disaccharides, trisaccharides, polysaccharides, oligosaccharides, and saccharide derivatives. Preferably the saccharide is selected from rhamnose, glucose, digitoxose, digitalose, digginose, sarmentose, vallarose, and fructose. Derivatives thereof, including sugar glycosides, N-glycosylamines, O-acyl derivatives, O-methyl derivatives, sugar alcohols, sugar acids, deoxy sugars, and related groups, are also preferred sugar groups.

Suitable halogen groups in the compounds of the present invention include F, Cl, Br and I.

The groups above mentioned may be substituted at one or more available positions by one or more suitable groups such as OR', =O, SR', SOR', $SO_2R'$, $NO_2$, NHR', $N(R')_2$, =N—R', NHCOR', $N(COR')_2$, $NHSO_2R'$, NR'C(=NR') NR'R', CN, halogen, COR', COOR', OCOR', OCONHR', $OCON(R')_2$, CONHR', $CON(R')_2$, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group, wherein each of the R' groups is independently selected from the group consisting of hydrogen, OH, $NO_2$, $NH_2$, SH, CN, halogen, COH, COalkyl, COOH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group. Where such groups are themselves substituted, the substituents may be chosen from the foregoing list.

The term "pharmaceutically acceptable salts and prodrugs" refers to any pharmaceutically acceptable salt, ester, solvate, hydrate or any other compound which, upon administration to the patient is capable of providing (directly or indirectly) a compound as described herein. However, it will be appreciated that non-pharmaceutically acceptable salts also fall within the scope of the invention since those may be useful in the preparation of pharmaceutically acceptable salts. The preparation of salts and prodrugs can be carried out by methods known in the art.

For instance, pharmaceutically acceptable salts of compounds provided herein are synthesized from the parent compound, which contains a basic or acidic moiety, by conventional chemical methods. Generally, such salts are, for example, prepared by reacting the free acid or base forms of these compounds with a stoichiometric amount of the appropriate base or acid in water or in an organic solvent or in a mixture of both. Generally, nonaqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, trifluoroacetate, maleate, fumarate, citrate, oxalate, succinate, tartrate, malate, mandelate, methanesulfonate and p-toluenesulfonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine and basic aminoacids salts.

The compounds of the invention may be in crystalline form either as free compounds or as solvates (e.g. hydrates) and it is intended that both forms are within the scope of the present invention. Methods of solvation are generally known within the art.

Any compound that is a prodrug of a compound of formula I is within the scope of the invention. The term "prodrug" is used in its broadest sense and encompasses those derivatives that are converted in vivo to the compounds of the invention. Examples of prodrugs include, but are not limited to, derivatives and metabolites of the compounds of formula I or II that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Preferably, prodrugs of compounds with carboxyl functional groups are the lower alkyl esters of the carboxylic acid. The carboxylate esters are conveniently formed by esterifying any of the carboxylic acid moieties present on the molecule. Prodrugs can tipically be prepared using well-known methods, such as those described by Burger "Medicinal Chemistry and Drug Discovery 6th ed. (Donald J. Abraham ed., 2001, Wiley) and "Design and Applications of Prodrugs" (H. Bundgaard ed., 1985, Harwood Academic Publishers).

Any compound referred to herein is intended to represent such specific compound as well as certain variations or forms. In particular, compounds referred to herein may have asymmetric centres and therefore exist in different enantiomeric or diastereoisomeric forms. Thus any given compound referred to herein is intended to represent any one of a racemate, one or more enantiomeric forms, one or more diastereomeric forms, and mixtures thereof. Likewise, stereoisomerism or geometric isomerism about the double bond is also possible, therefore in some cases the molecule could exist as (E)-isomer or (Z)-isomer (trans and cis isomers). If the molecule contains several double bonds, each double bond will have its own stereoisomerism, that could be the same as, or different to, the stereoisomerism of the other double bonds of the molecule. Furthermore, compounds referred to herein may exists as atropoisomers. All the stereoisomers including enantiomers, diastereoisomers, geometric isomers and atropoisomers of the compounds referred to herein, and mixtures thereof, are considered within the scope of the present invention.

Furthermore, any compound referred to herein may exist in isotopically-labelled forms i.e. compounds which differ in the presence of one or more isotopically-enriched atoms. For example, compounds having the present structures except for the replacement of at least one hydrogen atom by deuterium or tritium, or the replacement of at least one carbon by $^{13}$C— or $^{14}$C-enriched carbon, or the replacement of at least one nitrogen atom by $^{15}$N-enriched nitrogen are within the scope of this invention.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

In compounds of general formula I, each $R_1$ and $R_2$ is preferably and independently selected from hydrogen, halogen, $OR_a$, and $OCOR_a$, wherein $R_a$ is selected from hydrogen and substituted or unsubstituted $C_1$-$C_{12}$ alkyl. Particularly preferred $R_a$ is hydrogen and substituted or unsubstituted $C_1$-$C_6$ alkyl; and even more preferred is hydrogen, methyl, ethyl, n-propyl, isopropyl and butyl, including n-butyl, tert-butyl, sec-butyl and isobutyl. More preferably, $R_1$ and $R_2$ are each independently selected from hydrogen and halogen, being Cl the most preferred halogen.

Particular preferred $R_3$, $R_5$, $R_6$, $R_{14}$, and $R_{15}$ are each independently selected from hydrogen, $OR_a$, and $OCOR_a$, wherein $R_a$ is selected from hydrogen and substituted or unsubstituted $C_1$-$C_{12}$ alkyl. Particularly preferred $R_a$ is hydrogen and substituted or unsubstituted $C_1$-$C_6$ alkyl; and even more preferred is hydrogen, methyl, ethyl, n-propyl, isopropyl and butyl, including n-butyl, tert-butyl, sec-butyl and isobutyl. More preferably $R_3$, $R_5$, $R_6$, $R_{14}$, and $R_{15}$ are hydrogen.

$R_4$ is preferably selected from hydrogen and $OR_a$, wherein $R_a$ is selected from hydrogen and substituted or unsubstituted $C_1$-$C_{12}$ alkyl. Particularly preferred $R_a$ is hydrogen and substituted or unsubstituted $C_1$-$C_6$ alkyl; and even more preferred is hydrogen, methyl, ethyl, n-propyl, isopropyl and butyl, including n-butyl, tert-butyl, sec-butyl and isobutyl. More preferably, $R_4$ is $OR_a$ and $R_a$ is hydrogen.

$R_7$ is preferably selected from hydrogen, $OR_a$, and $OCOR_a$, wherein $R_a$ is selected from hydrogen and substituted or unsubstituted $C_1$-$C_{12}$ alkyl. Particularly preferred $R_a$ is hydrogen and substituted or unsubstituted $C_1$-$C_6$ alkyl; and even more preferred is hydrogen, methyl, ethyl, n-propyl, isopropyl and butyl, including n-butyl, tert-butyl, sec-butyl and isobutyl. More preferably, $R_7$ is hydrogen.

Particularly preferred $R_8$ and $R_9$ are each independently selected from hydrogen, substituted or unsubstituted $C_1$-$C_{12}$ alkyl, $OR_a$, and $OCOR_a$, wherein $R_a$ is selected from hydrogen and substituted or unsubstituted $C_1$-$C_{12}$ alkyl. Particularly preferred $R_a$ is hydrogen and substituted or unsubstituted $C_1$-$C_6$ alkyl; and even more preferred is hydrogen, methyl, ethyl, n-propyl, isopropyl and butyl, including n-butyl, tert-butyl, sec-butyl and isobutyl. More preferably $R_8$ and $R_9$ are each a substituted or unsubstituted $C_1$-$C_6$ alkyl; and even more preferred are methyl, ethyl, n-propyl, isopropyl and butyl, including n-butyl, tert-butyl, sec-butyl and isobutyl; being methyl the most preferred.

$R_{10}$ is preferably selected from $OR_b$, $OCOR_a$, and =O, with the proviso that when $R_{10}$ is =O the hydrogen of the C atom to which $R_{10}$ is attached is absent, and wherein $R_a$ is selected from hydrogen and substituted or unsubstituted $C_1$-$C_{12}$ alkyl and $R_b$ is selected from hydrogen, substituted or unsubstituted $C_1$-$C_{12}$ alkyl, and substituted or unsubstituted sugar. Particularly preferred $R_a$ is hydrogen and substituted or unsubstituted $C_1$-$C_6$ alkyl; and even more preferred is hydrogen, methyl, ethyl, n-propyl, isopropyl and butyl, including n-butyl, tert-butyl, sec-butyl and isobutyl. Particularly preferred $R_b$ is hydrogen, substituted or unsubstituted $C_1$-$C_6$ alkyl, monosaccharide, disaccharide, and trisaccharide; and even more preferred is hydrogen, methyl, ethyl, n-propyl, isopropyl, n-butyl, tert-butyl, sec-butyl, isobutyl, rhamnose, glucose, digitoxose, digitalose, digginose, sarmentose, vallarose, and fructose. More preferably, $R_{10}$ is =O or $OR_b$, wherein $R_b$ is methyl.

In one preferred class of the compounds of the invention wherein the ------- line is absent, particularly preferred $R_{11}$ and $R_{12}$ are each independently selected from hydrogen, $OR_a$, and $OCOR_a$, wherein $R_a$ is selected from hydrogen and substituted or unsubstituted $C_1$-$C_{12}$ alkyl. Particularly preferred $R_a$ is hydrogen and substituted or unsubstituted $C_1$-$C_6$ alkyl; and even more preferred is hydrogen, methyl, ethyl, n-propyl, isopropyl and butyl, including n-butyl, tert-butyl, sec-butyl and isobutyl.

In another preferred class of compounds of the invention wherein either an additional bond or an epoxy group is present in the place indicated with the ------- line, particularly preferred $R_{11}$ and $R_{12}$ are hydrogen.

$R_{13}$ is preferably selected from hydrogen, substituted or unsubstituted $C_1$-$C_{12}$ alkyl, and $COR_a$, wherein $R_a$ is selected from hydrogen and substituted or unsubstituted $C_1$-$C_{12}$ alkyl. Particularly preferred $R_a$ is hydrogen and substituted or unsubstituted $C_1$-$C_6$ alkyl; and even more preferred is hydrogen, methyl, ethyl, n-propyl, isopropyl and butyl, including n-butyl, tert-butyl, sec-butyl and isobutyl. More preferably $R_{13}$ is substituted or unsubstituted $C_1$-$C_6$ alkyl and $COR_a$, wherein $R_a$ is hydrogen and substituted or unsubstituted $C_1$-$C_6$ alkyl. Even more preferred $R_{13}$ is a substituted or unsubstituted methyl, substituted or unsubstituted ethyl, substituted or unsubstituted propyl, and $COR_a$, wherein $R_a$ is hydrogen. Preferred substituents of methyl, ethyl, and propyl are OR' wherein R' is hydrogen or COalkyl, being hydrogen the most preferred R'.

$R_{16}$ is preferably selected from hydrogen, $OR_a$, and $OCOR_a$, wherein $R_a$ is selected from hydrogen and substituted or unsubstituted $C_1$-$C_{12}$ alkyl. Particularly preferred $R_a$ is hydrogen and substituted or unsubstituted $C_1$-$C_6$ alkyl; and even more preferred is hydrogen, methyl, ethyl, n-propyl, isopropyl and butyl, including n-butyl, tert-butyl, sec-butyl and isobutyl. More preferably $R_{16}$ is hydrogen or $OR_a$, wherein $R_a$ is hydrogen.

Particularly preferred $R_{17}$ is substituted or unsubstituted $C_1$-$C_{12}$ alkyl. More preferably is a substituted or unsubstituted $C_1$-$C_6$ alkyl; and even more preferred is methyl, ethyl, n-propyl, isopropyl and butyl, including n-butyl, tert-butyl, sec-butyl and isobutyl. Methyl is the most preferred $R_{17}$.

Particularly preferred is the presence of an additional bond or an epoxy group in the place indicated with the ------- line.

More particularly, the invention provides compounds of general formula II or pharmaceutically acceptable salts, prodrugs or stereoisomers thereof

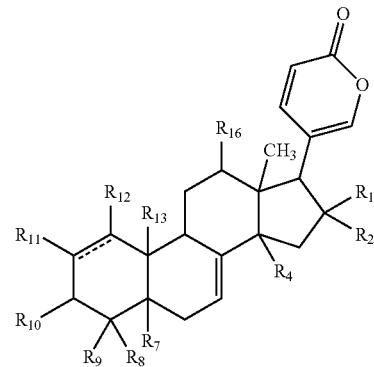

wherein $R_1$, $R_2$, $R_4$, $R_7$, $R_8$-$R_{13}$, $R_{16}$ and the ------- line have the same meaning given above.

Particularly preferred stereochemistry of said compounds of general formula II is the following:

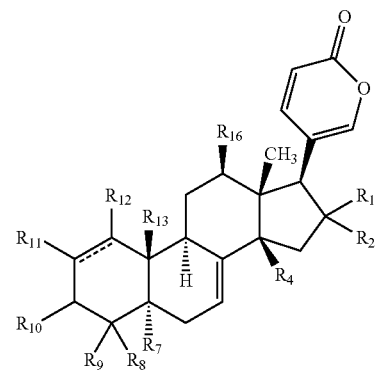

In compounds of general formula II, each $R_1$ and $R_2$ is preferably and independently selected from hydrogen, halogen, $OR_a$, and $OCOR_a$, wherein $R_a$ is selected from hydrogen and substituted or unsubstituted $C_1$-$C_{12}$ alkyl. Particularly preferred $R_a$ is hydrogen and substituted or unsubstituted $C_1$-$C_6$ alkyl; and even more preferred is hydrogen, methyl, ethyl, n-propyl, isopropyl and butyl, including n-butyl, tert-butyl, sec-butyl and isobutyl. More preferably, $R_1$ and $R_2$ are each independently selected from hydrogen and halogen, being Cl the most preferred halogen.

$R_4$ is preferably selected from hydrogen and $OR_a$, wherein $R_a$ is selected from hydrogen and substituted or unsubstituted $C_1$-$C_{12}$ alkyl. Particularly preferred $R_a$ is hydrogen and substituted or unsubstituted $C_1$-$C_6$ alkyl; and even more preferred is hydrogen, methyl, ethyl, n-propyl, isopropyl and butyl, including n-butyl, tert-butyl, sec-butyl and isobutyl. More preferably, $R_4$ is $OR_a$ and $R_a$ is hydrogen.

$R_7$ is preferably selected from hydrogen, $OR_a$, and $OCOR_a$, wherein $R_a$ is selected from hydrogen and substituted or unsubstituted $C_1$-$C_{12}$ alkyl. Particularly preferred $R_a$ is hydrogen and substituted or unsubstituted $C_1$-$C_6$ alkyl; and even more preferred is hydrogen, methyl, ethyl, n-propyl, isopropyl and butyl, including n-butyl, tert-butyl, sec-butyl and isobutyl. More preferably, $R_7$ is hydrogen.

Particularly preferred $R_8$ and $R_9$ are each independently selected from hydrogen, substituted or unsubstituted $C_1$-$C_{12}$ alkyl, $OR_a$, and $OCOR_a$, wherein $R_a$ is selected from hydrogen and substituted or unsubstituted $C_1$-$C_{12}$ alkyl. Particularly preferred $R_a$ is hydrogen and substituted or unsubstituted $C_1$-$C_6$ alkyl; and even more preferred is hydrogen, methyl, ethyl, n-propyl, isopropyl and butyl, including n-butyl, tert-butyl, sec-butyl and isobutyl. More preferably $R_8$ and $R_9$ are each a substituted or unsubstituted $C_1$-$C_6$ alkyl; and even more preferred are methyl, ethyl, n-propyl, isopropyl and butyl, including n-butyl, tert-butyl, sec-butyl and isobutyl; being methyl the most preferred.

$R_{10}$ is preferably selected from $OR_b$, and $OCOR_a$, and =O, with the proviso that when $R_{10}$ is =O the hydrogen of the C atom to which $R_{10}$ is attached is absent, and wherein $R_a$ is selected from hydrogen and substituted or unsubstituted $C_1$-$C_{12}$ alkyl and $R_b$ is selected from hydrogen, substituted or unsubstituted $C_1$-$C_{12}$ alkyl, and substituted or unsubstituted sugar. Particularly preferred $R_a$ is hydrogen and substituted or unsubstituted $C_1$-$C_6$ alkyl; and even more preferred is hydrogen, methyl, ethyl, n-propyl, isopropyl and butyl, including n-butyl, tert-butyl, sec-butyl and isobutyl. Particularly preferred $R_b$ is hydrogen, substituted or unsubstituted $C_1$-$C_6$ alkyl, monosaccharide, disaccharide, and trisaccharide; and even more preferred is hydrogen, methyl, ethyl, n-propyl, isopropyl, n-butyl, tert-butyl, sec-butyl, isobutyl, rhamnose, glucose, digitoxose, digitalose, digginose, sarmentose, vallarose, and fructose. More preferably, $R_{10}$ is =O or $OR_b$, wherein $R_b$ is methyl.

In one preferred class of the compounds of the invention wherein the ------- line is absent, particularly preferred $R_{11}$ and $R_{12}$ are each independently selected from hydrogen, $OR_a$, and $OCOR_a$, wherein $R_a$ is selected from hydrogen and substituted or unsubstituted $C_1$-$C_{12}$ alkyl. Particularly preferred $R_a$ is hydrogen and substituted or unsubstituted $C_1$-$C_6$ alkyl; and even more preferred is hydrogen, methyl, ethyl, n-propyl, isopropyl and butyl, including n-butyl, tert-butyl, sec-butyl and isobutyl.

In another preferred class of compounds of the invention wherein either an additional bond or an epoxy group is present in the place indicated with the ------- line, particularly preferred $R_{11}$ and $R_{12}$ are hydrogen.

$R_{13}$ is preferably selected from hydrogen, substituted or unsubstituted $C_1$-$C_{12}$ alkyl, and $COR_a$, wherein $R_a$ is selected from hydrogen and substituted or unsubstituted $C_1$-$C_{12}$ alkyl. Particularly preferred $R_a$ is hydrogen and substituted or unsubstituted $C_1$-$C_6$ alkyl; and even more preferred is hydrogen, methyl, ethyl, n-propyl, isopropyl and butyl, including n-butyl, tert-butyl, sec-butyl and isobutyl. More preferably $R_{13}$ is substituted or unsubstituted $C_1$-$C_6$ alkyl and $COR_a$, wherein $R_a$ is hydrogen and substituted or unsubstituted $C_1$-$C_6$ alkyl. Even more preferred $R_{13}$ is a substituted or unsubstituted methyl, substituted or unsubstituted ethyl, substituted or unsubstituted propyl, and $COR_a$, wherein $R_a$ is hydrogen. Preferred substituents of methyl, ethyl, and propyl are OR' wherein R' is hydrogen or COalkyl, being hydrogen the most preferred R'.

$R_{16}$ is preferably selected from hydrogen, $OR_a$, and $OCOR_a$, wherein $R_a$ is selected from hydrogen and substituted or unsubstituted $C_1$-$C_{12}$ alkyl. Particularly preferred $R_a$ is hydrogen and substituted or unsubstituted $C_1$-$C_6$ alkyl; and even more preferred is hydrogen, methyl, ethyl, n-propyl, isopropyl and butyl, including n-butyl, tert-butyl, sec-butyl and isobutyl. More preferably $R_{16}$ is hydrogen or $OR_a$, wherein $R_a$ is hydrogen.

Particularly preferred is the presence of an additional bond or an epoxy group in the place indicated with a ------- line.

In the present description and definitions, when there are several substituents $R_a$ present in the compounds of the invention, and unless it is stated explicitly so, it should be understood that they can be each independently different within the given definition, i.e. $R_a$ does not represent necessarily the same group simultaneously in a given compound of the invention.

In the previous paragraphs preferences for the substituent groups $R_1$ to $R_{17}$ and the dotted line are defined. It should also be understood that the different combinations of these preferences are also preferred within the compounds of the invention.

Particularly preferred compounds of the invention are the following:

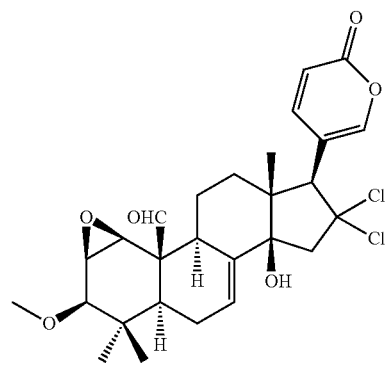

Aegomycin A

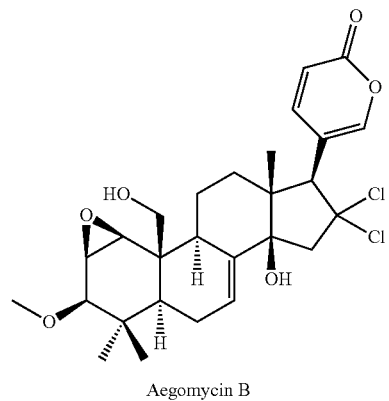

Aegomycin B

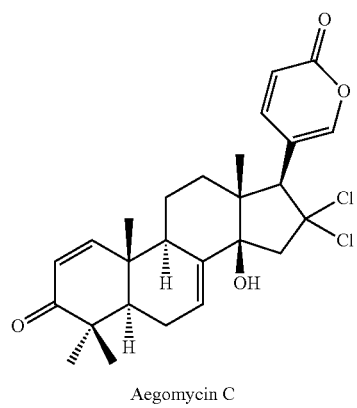

Aegomycin C

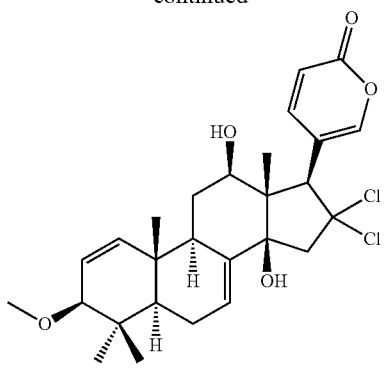

Aegomycin D

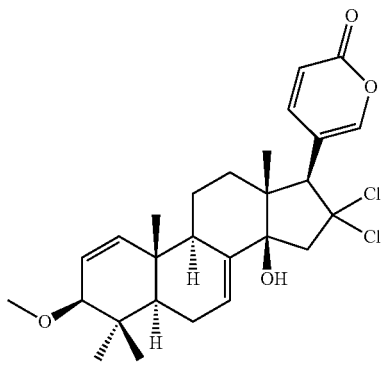

Aegomycin E

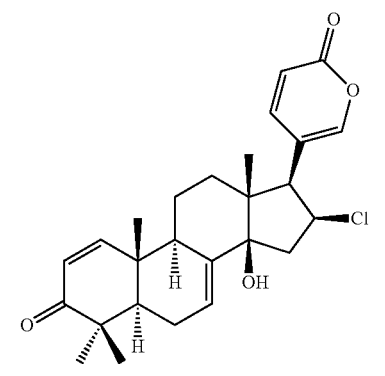

Aegomycin F

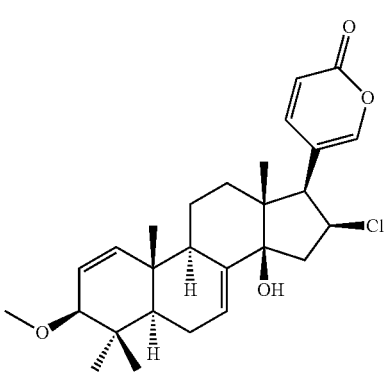

Aegomycin G

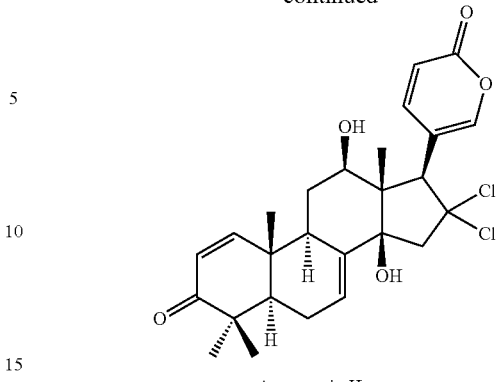

Aegomycin H or pharmaceutically acceptable salts, prodrugs or stereoisomers thereof. The stereochemistry indicated here for Aegomycins A-H is relative.

Aegomycins A-H were isolated from a porifera of the family Mycalidae, genus *Mycale*, subgenus *Aegogropila*, species *Mycale* (*Aegogropila*) *crassissima* (Dendy, 1905). A sample of *Mycale* (*Aegogropila*) *crassissima* (Dendy, 1905) was deposited at the Institute of Marine Sciences and Limnology of the Universidad Nacional Autónoma of Mexico, with the reference code MHA-399. This sponge was collected by hand using SCUBA diving in Mafia Island (07° 39.558' S/39° 55.043' E) at depths ranging between 5 and 31.4 m.

The description of the sponge is the following: The specimens examined were thinly encrusting growing on rocks. The colour of live specimens was brown, although they have also been described as orange or ochre. Spicule complement: Megascleres were straight subtylostyles, often with hardly perceptible tyle, and usually slightly bent in the middle. They had about 270 µm of mean length, about 4.6 µm of shaft width and about 4.8 µm of tyle width. Microscleres included palmate anisochelae (three size classes: Anisochela 1 of about 36 µm in average, anisochela 2 of about 27 µm in average, and anisochela 3 of about 11 µm in average), sigmas (one class: Robust sigma of about 57 µm in average), and raphides (very scarce). Skeletal arrangement: Tracts of subtylostyles ascended outwards from the basal plate and terminated at the surface in slight tufts or brushes. Ectosome had a well developed reticulation of bundles of mycalostyles and microscleres were strewn at random in both choanosome and ectosome. The anisochelae did not form rosettes. *Mycale crassissima* is common in the collected area of Mafia Island and has also been found in Mombassa, Zanzibar, Madagascar, Ceylon, and Arafura Sea, on rocks and coral reefs, from 1 to 60 m depth.

Additionally, compounds of the invention can be obtained by synthesis following usual procedures in synthetic organic chemistry and already known by a person skilled in the art. For example, compounds of this invention can be obtained adapting the procedures described in the literature such as in Steyn et al. Nat. Prod. Rep. 1998, 15, 397-413; Huimin Gao et al in Nat. Prod. Rep., 2011, 28, 953; WO 01/79256; WO 2006/120472; and CA 2.418.458. The synthetic routes can use combinations of steps taken from more than one of these references.

Likewise, natural, synthetic or already modified compounds of the invention can be further modified by a variety of chemical reaction to obtain additional compounds of the invention. Thus, hydroxyl groups can be acylated by standard coupling or acylation procedures, for instance by using acetic acid or acetic anhydride in pyridine or the like. Formate groups can be obtained by heating hydroxyl precursors in formic acid. Hydroxy groups can also be oxidized to oxo (=O), for instance, by using manganese dioxide or chromium, or converted into amino-lower alkoxy, for instance, by using a protected 2-bromoethylamine. Carboxy groups can be alkylated, for instance, methylated by treatment with diazomethane. Glycosidic moieties can be introduced by standard sugar coupling reactions.

An important feature of the above described compounds of formula I and II is their bioactivity and in particular their cytotoxic activity.

With this invention we provide novel pharmaceutical compositions of compounds of general formula I and II that possess cytotoxic activity and their use as anticancer agents. Thus the present invention further provides pharmaceutical compositions comprising a compound of this invention, or a pharmaceutically acceptable salt, prodrug or stereoisomer thereof with a pharmaceutically acceptable carrier.

Examples of pharmaceutical compositions include any solid (tablets, pills, capsules, granules etc.) or liquid (solutions, suspensions or emulsions) composition for oral, topical or parenteral administration.

Administration of the compounds or compositions of the present invention may be by any suitable method, such as intravenous infusion, oral preparations, and intraperitoneal and intravenous administration. We prefer that infusion times of up to 24 hours are used, more preferably 1-12 hours, with 1-6 hours most preferred. Short infusion times which allow treatment to be carried out without an overnight stay in hospital are especially desirable. However, infusion may be 12 to 24 hours or even longer if required. Infusion may be carried out at suitable intervals of say 1 to 4 weeks. Pharmaceutical compositions containing compounds of the invention may be delivered by liposome or nanosphere encapsulation, in sustained release formulations or by other standard delivery means.

The correct dosage of the compounds will vary according to the particular formulation, the mode of application, and the particular situs, host and tumour being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

As used herein, the terms "treat", "treating" and "treatment" include the eradication, removal, modification, or control of a tumor or primary, regional, or metastatic cancer cells or tissue and the minimization or delay of the spread of cancer.

The compounds of the invention have activity against cancers including, but not limited, lung cancer, colon cancer, and breast cancer.

EXAMPLES

Example 1

Description of the Marine Organism and Collection Site

*Mycale* (*Aegogropila*) *crassissima* (Dendy, 1905) was collected by hand using SCUBA diving in Mafia Island (07° 39.558' S/39° 55.043' E) at depths ranging between 5 and 31.4 m. The animal material was identified by Dr. José Luis Carballo (Universidad Nacional Autónoma of Mexico). A sample of the specimen was deposited at the Institute of Marine Sciences and Limnology of the Universidad Nacional Autónoma of Mexico, with the reference code MFIA-399.

Example 2

Isolation of Aegomycins A and B

The frozen specimen of Example 1 (67 g) was triturated and extracted with $H_2O$ and a mixture of $MeOH:CH_2Cl_2$ (50:50) at 23° C. The organic extract was evaporated under reduced pressure to yield a crude of 500 mg. This material was chromatographed (VLC) on Lichroprep RP-18 with a stepped gradient from $H_2O$ to MeOH and $CH_2Cl_2$. Two fractions obtained from this chromatography were further purified as described below. The fraction eluted with $H_2O$:MeOH 1:3 (23 mg) was subjected to semipreparative reversed phase HPLC (Symmetry Prep C18, 7.8×150 mm, gradient $H_2O$: MeCN from 60 to 75% of MeCN in 10 min then 75 to 100% of MeCN in 10 min, UV detection, flow 2.3 mL/min) to yield Aegomycin A (0.6 mg). The fraction eluted with MeOH (83 mg) was subjected to semipreparative reversed phase HPLC (Symmetry Prep C18, 7.8×150 mm, gradient $H_2O$:MeCN from 50 to 75% of MeCN in 30 min, UV detection, flow 2.3 mL/min) to yield Aegomycin A (1.8 mg) and Aegomycin B (0.8 mg).

Aegomycin A: amorphous white solid. (+)HRMALDIMS m/z 523.1622 $[M+H]^+$ (Calcd. for $C_{27}H_{33}{}^{35}Cl_2O_6$ 523.1649); $^1H$ (500 MHz) and $^{13}C$ NMR (75 MHz) in $CDCl_3$ see Table 1

Aegomycin B: amorphous white solid. (+)HRMALDIMS m/z 525.1788 $[M+H]^+$ (Calcd. for $C_{27}H_{35}{}^{35}Cl_2O_6$ 525.1805); $^1H$ (500 MHz) and $^{13}C$ NMR (75 MHz) in $CD_3OD$ see Table 2.

TABLE 1

$^1H$ and $^{13}C$ NMR data of Aegomycin A ($CDCl_3$).

| N° | $^1H$, m, J (Hz) | $^{13}C$, m | HMBC | ROESY |
|---|---|---|---|---|
| 1 | 3.74, d (3.8) | 54.3, d | C5, C9, C10, C19 | H2, H11a |
| 2 | 3.25, d (3.8) | 55.7, d | C3, C4 | OMe, H1, H3 |
| 3 | 2.88, s | 84.4, d | C1, C2, C4, C20, C21, OMe | OMe, H2, H5, H20 |
| 4 | — | 36.7, s | — | — |
| 5 | 1.51, dd (10.6, 7.8) | 41.0, d | C4, C9, C10, C6, C19, C21 | H3, H6, H9, H20 |
| 6 | 2.40, m | 22.7, t | C7 | H5, H7, H19, H20, H21 |
| 7 | 6.19, m | 122.8, d | — | H6, 14-OH |
| 8 | — | 137.5, s | — | — |
| 9 | 2.62, m | 41.1, d | — | H5, H11a, H12a, H15a |
| 10 | — | 49.8, s | — | — |
| 11a | 1.90, m | 22.7, t | C8 | H1, H9, H11b |
| 11b | 1.25, m | | C9 | H11a, H12b, H18, H19 |
| 12a | 1.89, m | 39.3, t | C13, C14, C15, C18 | H9, H12b, H15a, H17 |
| 12b | 1.72, m | | C13 | H11b, H12a, H17, H18 |
| 13 | — | 51.0, s | — | — |
| 14 | — | 83.8, s | — | — |
| 14-OH | 1.87, m | — | C14 | H7, H18 |
| 15a | 3.47, d (15.8) | 62.0 t | C13, C14, C16 | H9, H12a, H15b |
| 15b | 2.81, d (15.8) | | C13, C14, C16, C17 | H15a |
| 16 | — | 92.5, s | — | — |
| 17 | 3.46, s | 71.2, d | C12, C13, C16, C22, C23, C24 | H12a, H12b, H23 |
| 18 | 0.74, s | 16.5, q | C12, C13, C14, C17 | H11b, H12b, H24, 14-OH |
| 19 | 9.87, s | 205.6, d | C1, C10 | H6, H11b, H21 |

TABLE 1-continued $^1$H and $^{13}$C NMR data of Aegomycin A (CDCl$_3$).

| N° | $^1$H, m, J (Hz) | $^{13}$C, m | HMBC | ROESY |
|---|---|---|---|---|
| 20 | 0.94, s | 25.0, q | C3, C4, C5, C21 | OMe, H3, H5, H6, H21 |
| 21 | 0.66, s | 16.2, q | C3, C4, C5, C20 | H6, H19, H20 |
| 22 | — | 116.7, s | — | — |
| 23 | 7.33, d (2.7) | 151.0, d | C17, C22, C24 | H17 |
| 24 | 8.00, dd (9.9, 2.7) | 147.9, d | C26 | H18, H25 |
| 25 | 6.28, d (9.9) | 113.9, d | C22, C26 | H24 |
| 26 | — | 161.4, s | — | — |
| OMe | 3.51, s | 58.3, q | C3 | H2, H3, H20 |

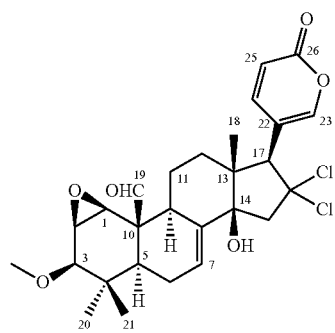

Aegomycin A

TABLE 2

$^1$H and $^{13}$C NMR data of Aegomycin B (CD$_3$OD).

| N° | $^1$H, m, J (Hz) | $^{13}$C, m | HMBC | ROESY |
|---|---|---|---|---|
| 1 | 3.74, d (3.7) | 56.6, d | C5, C10 | H2, H11 |
| 2 | 3.18, d (3.7) | 57.5, d | C3, C4 | OMe, H1, H3 |
| 3 | 2.85, s | 87.0, d | OMe, C1, C2, C4, C5, C20, C21 | OMe, H2, H5, H20 |
| 4 | — | 37.6, s | — | — |
| 5 | 1.05, dd (12.4, 5.0) | 43.2, d | C3, C4, C6, C9, C10, C19, C21 | H3, H9, H20 |
| 6 | 1.99, m | 22.7, t | C7, C8 | H7, H20 |
| 7 | 6.05, m | 124.6, d | — | H6 |
| 8 | — | 139.6, s | — | — |
| 9 | 2.42, m | 46.1, d | — | H5, H15a |
| 10 | — | 40.0, s | — | — |
| 11 | 1.90, m | 23.5, t | C12 | H1, H18 |
| 12 | 1.79, m | 40.7, t | C11 | H17, H18 |
| 13 | — | 52.6, s | — | — |
| 14 | — | 84.7, s | — | — |
| 15a | 3.43, d (15.8) | 64.1, t | C8, C13, C14, C16 | H9, H15b |
| 15b | 2.76, d (15.8) | | C14, C16, C17 | H15a |
| 16 | — | 94.9, s | — | — |
| 17 | 3.61, s | 72.8, d | C12, C13, C14, C16, C22, C24, C25 | H12, H23 |
| 18 | 0.79, s | 17.3, q | C12, C13, C14, C17 | H11, H12, H24 |
| 19a | 3.98, d (12.1) | 60.7, t | C1, C5, C9, C10 | H19b, H21 |
| 19b | 3.75, d (12.1) | | C1, C5, C9, C10 | H19a |
| 20 | 0.89, s | 26.4, q | C3, C4, C5, C21 | H3, H5, H6 |
| 21 | 0.92, s | 17.3, q | C3, C4, C5, C20 | H19a |
| 22 | — | 119.8, s | — | — |
| 23 | 7.57, d (2.2) | 152.9, d | C17, C22, C24, C26 | H17 |
| 24 | 8.30, dd (9.8, 2.2) | 151.5, d | C23, C26 | H18, H25 |
| 25 | 6.28, d (9.8) | 113.7, d | C22, C26 | H24 |
| 26 | — | 164.1, s | — | — |
| OMe | 3.49, s | 58.4, q | C3 | H2, H3 |

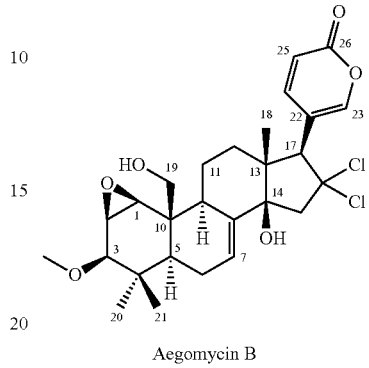

Aegomycin B

Example 3

Isolation of Aegomycins C, D, E, F and G

A second group of samples of the specimen of Example 1 (160 g) was triturated and extracted with H$_2$O and a mixture of MeOH:CH$_2$Cl$_2$ (50:50) at 23° C. The organic extract was evaporated under reduced pressure to yield a crude of 3.12 g. This material was chromatographed (VLC) on Lichroprep RP-18 with a stepped gradient from H$_2$O to MeOH and CH$_2$Cl$_2$. Two fractions obtained from this chromatography were further purified as described below. The fraction eluted with H$_2$O:MeOH 1:3 (122 mg) was subjected to semipreparative reversed phase HPLC (Symmetry Prep C18, 7.8×150 mm, gradient H$_2$O:MeCN from 45 to 65% of MeCN in 30 min, UV detection, flow 2.3 mL/min) to yield Aegomycin F (2.6 mg) and a mixture of other Aegomycin compounds (5.1 mg). This mixture was further purified by semipreparative HPLC(X Terra Phenyl, 10×150 mm, gradient H$_2$O:MeCN from 45 to 60% of MeCN in 30 min, UV detection, flow 2.3 mL/min) to yield Aegomycin C (0.5 mg) and D (2.8 mg). The fraction eluted with MeOH (230 mg) was subjected to flash Silica gel CC eluting with a gradient of hexane:EtOAc to yield 11 fractions (S1 to S11). Fractions S6 (hexane:EtOAc 70:30) and S7 (hexane:EtOAc 60:40) were subjected to semi-preparative reversed phase HPLC(X Terra Phenyl, 10×150 mm, gradient H$_2$O:MeCN from 50 to 55% of MeCN in 30 min, UV detection, flow 3.0 mL/min) to yield Aegomycin E (1.3 mg) from S6 and Aegomycin G (0.3 mg) from S7.

Aegomycin C: amorphous white solid. (+)HRMALDIMS m/z 477.1581 [M+H]$^+$ (Calcd. for C$_{26}$H$_{31}$$^{35}$Cl$_2$O$_4$ 477.1594); $^1$H (500 MHz) and $^{13}$C NMR (75 MHz) in CD$_3$OD see Table 3.

Aegomycin D: amorphous white solid. (+)HRMALDIMS m/z 509.1834 [M+H]$^+$ (Calcd. for C$_{27}$H$_{35}$$^{35}$Cl$_2$O$_5$ 509.1856); $^1$H (500 MHz) and $^{13}$C NMR (125 MHz) in CD$_3$OD see Table 4.

Aegomycin E: amorphous white solid. (+)HRMALDIMS m/z 493.1898 [M+H]$^+$(Calcd. for C$_{27}$H$_{35}$$^{35}$Cl$_2$O$_4$ 493.1907); $^1$H (500 MHz) and $^{13}$C NMR (75 MHz) in CD$_3$OD see Table 5.

Aegomycin F: amorphous white solid. (+)HRMALDIMS m/z 443.1997 [M+H]$^+$ (Calcd. for C$_{26}$H$_{32}$$^{35}$ClO$_4$ 443.1984); $^1$H (500 MHz) and $^{13}$C NMR (75 MHz) in CD$_3$OD see Table 6.

Aegomycin G: amorphous white solid. (+)HRMALDIMS m/z 459.2306 [M+H]$^+$ (Calcd. for $C_{27}H_{36}{}^{35}ClO_4$ 459.2297); $^1$H (500 MHz) and $^{13}$C NMR (75 MHz) in $CD_3OD$ see Table 7.

TABLE 3

$^1$H and $^{13}$C NMR data of Aegomycin C (CD$_3$OD).

| N° | $^1$H, m, J (Hz) | $^{13}$C, m | HMBC | ROESY |
|---|---|---|---|---|
| 1 | 7.12, d (10.3) | 157.2, d | C3, C5, C10 | H2, H11a |
| 2 | 5.91, d (10.3) | 124.4, d | C4, C10 | H1 |
| 3 | — | 206.7, s | — | — |
| 4 | — | 44.9, s | — | — |
| 5 | 1.85, m | 48.9, d | C4, C6, C10, C19 | H6, H9, H20 |
| 6 | 2.17, m | 24.0, t | — | H5, H7, H9, H20 |
| 7 | 6.15, m | 124.4, d | C5, C14 | H6 |
| 8 | — | 138.4, s | — | — |
| 9 | 2.21, m | 46.9, d | — | H5, H6, H15a |
| 10 | — | 38.9, s | — | — |
| 11a | 1.87, m | 21.9, t | C19 | H1, H11b |
| 11b | 1.54, dddd (13.7, 13.7, 13.7, 3.4) | | — | H11a, H12b, H18, H19 |
| 12a | 1.96, ddd (13.7, 13.7, 3.4) | 40.3, t | — | H12b, H15a, H17 |
| 12b | 1.79, ddd (13.7, 3.4, 3.4) | | C18 | H11b, H12a, H17, H18 |
| 13 | — | 52.4, s | — | — |
| 14 | — | 84.7, s | — | — |
| 15a | 3.44, d (16.1) | 63.6, t | C8, C13, C14, C16 | H9, H12a, H15b |
| 15b | 2.78, d (16.1) | | C14, C16, C17 | H15a |
| 16 | — | 94.9, s | — | — |
| 17 | 3.62, s | 72.5, d | C12, C13, C14, C16, C22, C23 | H12a, H12b, H23 |
| 18 | 0.77, s | 17.2, q | C12, C13, C14, C17 | H11b, H12b |
| 19 | 1.07, s | 14.9, q | C1, C5, C9, C10 | H11b, H21 |
| 20 | 1.15, s | 24.0, q | C3, C4, C5, C21 | H5, H6 |
| 21 | 1.13, s | 22.5, q | C3, C4, C5, C20 | H19 |
| 22 | — | 119.7, s | — | — |
| 23 | 7.58, d (2.2) | 152.9, d | C22, C24, C26 | H17 |
| 24 | 8.32, dd (10.3, 2.2) | 151.4, d | C23, C26 | H25 |
| 25 | 6.29, d (10.3) | 113.7, d | C22, C26 | H24 |
| 26 | — | 164.1, s | — | — |

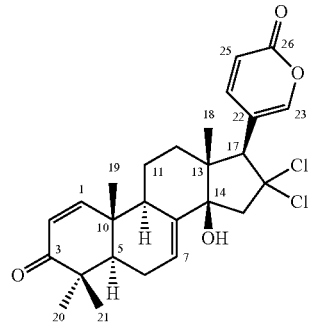

Aegomycin C

TABLE 4

$^1$H and $^{13}$C NMR data of Aegomycin D (CD$_3$OD).

| N° | $^1$H, m, J (Hz) | $^{13}$C, m | HMBC | ROESY |
|---|---|---|---|---|
| 1 | 5.82, dd (10.7, 2.4) | 135.3, d | C3, C5 | H2, H11a, H19 |
| 2 | 5.67, dd (10.7, 1.0) | 126.5, d | — | H1, OMe |
| 3 | 3.40, m | 87.3, d | OMe, C1, C2, C4, C20, C21 | H5, H20 |
| 4 | — | 37.7, s | — | — |
| 5 | 1.45, dd (11.9, 4.2) | 49.2, d | C3, C4, C6, C9, C10, C19, C21 | H3, H9, H20 |
| 6a | 2.14, m | 23.4, t | C7, C8 | H6b, H7, H20 |

TABLE 4-continued $^1$H and $^{13}$C NMR data of Aegomycin D (CD$_3$OD).

| N° | $^1$H, m, J (Hz) | $^{13}$C, m | HMBC | ROESY |
|---|---|---|---|---|
| 6b | 2.04, m | | — | H6a, H19, H21 |
| 7 | 6.12, m | 125.9, d | C5, C9, C14 | H6a |
| 8 | — | 137.9, s | — | — |
| 9 | 2.08, m | 46.8, d | C8, C10 | H5, H11a, H12, H15a |
| 10 | — | 38.4, s | — | — |
| 11a | 1.83, ddd (12.7, 4.4, 4.2) | 30.3, t | C8, C9, C12, C13 | H1, H9, H12, H11b |
| 11b | 1.53, ddd (12.7, 12.7, 11.9) | | C9, C10, C12, C13 | H11a, H18, H19 |
| 12 | 3.84, dd (11.9, 4.2) | 74.9, d | C17, C18 | H9, H11a, H15a, H17 |
| 13 | — | 58.3, s | — | — |
| 14 | — | 85.0, s | — | — |
| 15a | 3.28, d (16.1) | 64.0, t | C8, C14, C16 | H9, H12, H15b |
| 15b | 2.80, d (16.1) | | C13, C14, C16, C17 | H15a |
| 16 | — | 95.1, s | — | — |
| 17 | 4.15, s | 68.2, d | C12, C13, C14, C16, C22, C23, C24 | H12, H18, H23 |
| 18 | 0.65, s | 10.5, q | C12, C13, C14, C17 | H11b, H17, H19, H24 |
| 19 | 0.92, s | 15.3, q | C1, C5, C9, C10 | H1, H6b, H11b, H18, H21 |
| 20 | 0.99, s | 26.6, q | C3, C4, C5, C21 | H3, H5, H6a, H21 |
| 21 | 0.85, s | 17.2, q | C3, C4, C5, C20 | H6b, H19, H20 |
| 22 | — | 120.0, s | — | — |
| 23 | 7.54, d (2.9) | 156.0, d | C22, C24, C26 | H17 |
| 24 | 8.27, dd (9.8, 2.9) | 151.6, d | C23, C26 | H18, H25 |
| 25 | 6.28, d (9.8) | 113.7, d | C22, C26 | H24 |
| 26 | — | 164.1, s | — | — |
| OMe | 3.41, s | 58.3, q | C3 | H2 |

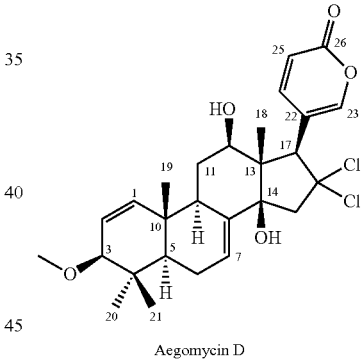

Aegomycin D

TABLE 5

$^1$H and $^{13}$C NMR data of Aegomycin E (CD$_3$OD).

| N° | $^1$H, m, J (Hz) | $^{13}$C, m | HMBC | ROESY |
|---|---|---|---|---|
| 1 | 5.83, dd (10.5, 2.3) | 135.7, d | C2, C5, C9 | H2, H11a, H19 |
| 2 | 5.65, dd (10.5, 1.5) | 126.2, d | C4 | H1, H3 |
| 3 | 3.40, m | 87.3, d | C1 | H2, H5, H20 |
| 4 | — | 37.7, s | — | — |
| 5 | 1.42, dd (12.0, 4.5) | 48.9, d | C19 | H3, H9, H20 |
| 6a | 2.12, m | 23.4, t | — | H6b, H7, H20 |
| 6b | 2.01, m | | — | H6a, H19, H21 |
| 7 | 6.11, br d (5.6) | 125.2, d | C5, C14 | H6a |
| 8 | — | 139.0, s | — | — |
| 9 | 2.02, m | 49.1, d | — | H5, H15a |
| 10 | — | 38.6, s | — | — |
| 11a | 1.71, m | 21.9, t | — | H1, H11b |
| 11b | 1.51, dddd (13.8, 13.7, 13.7, 3.4) | | — | H11a, H18, H19 |
| 12a | 1.90, ddd (13.7, 13.7, 3.4) | 40.5, t | — | H12b, H15a, H17 |

TABLE 5-continued $^1$H and $^{13}$C NMR data of Aegomycin E (CD$_3$OD).

| N° | $^1$H, m, J (Hz) | $^{13}$C, m | HMBC | ROESY |
|---|---|---|---|---|
| 12b | 1.74, m | | | H12a, H17 |
| 13 | — | 52.5, s | — | — |
| 14 | — | 84.8, s | — | — |
| 15a | 3.43, d (15.6) | 63.9, t | C16 | H9, H12a, H15b |
| 15b | 2.76, d (15.6) | | C14, C16, C17 | H15a |
| 16 | — | 95.0, s | — | — |
| 17 | 3.59, s | 72.6, d | C14, C16, C22, C23, C24 | H12a, H12b, H23 |
| 18 | 0.74, s | 17.2, q | C12, C13, C14, C17 | H11b, H24 |
| 19 | 0.91, s | 15.3, q | C1, C5, C9, C10 | H1, H6b, H11b, H21 |
| 20 | 0.99, s | 26.7, q | C3, C4, C5, C21 | H3, H5, H6a, H21 |
| 21 | 0.85, s | 17.2, q | C3, C4, C5, C20 | H6b, H19, H20 |
| 22 | — | 119.7, s | | |
| 23 | 7.57, d (2.4) | 152.8, d | C22 | H17 |
| 24 | 8.31, dd (9.8, 2.4) | 151.5, d | | H18, H25 |
| 25 | 6.28, d (9.8) | 113.7, d | C22, C26 | H24 |
| 26 | — | 164.1, s | — | — |
| OMe | 3.41, s | 58.3, q | C3 | — |

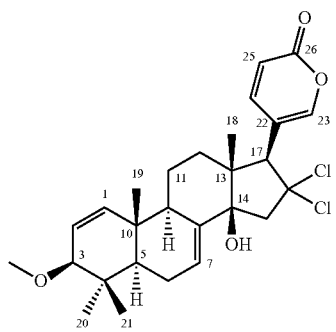

Aegomycin E

TABLE 6

$^1$H and $^{13}$C NMR data of Aegomycin F (CD$_3$OD).

| N° | $^1$H, m, J (Hz) | $^{13}$C, m | HMBC | ROESY |
|---|---|---|---|---|
| 1 | 7.10, d (10.3) | 157.5, d | C3, C5, C6, C9, C10, C19 | H2, H11a, H19 |
| 2 | 5.88, d (10.3) | 126.1, d | C4, C10, C19 | H1 |
| 3 | — | 206.8, s | — | — |
| 4 | — | 45.0, s | — | — |
| 5 | 1.83, dd (12.1, 4.2) | 48.5, d | C4, C6, C9, C19, C20, C21 | H6, H9, H20 |
| 6 | 2.18, m | 23.9, t | C7, C8 | H5, H7, H19, H20, H21 |
| 7 | 6.13, br d (5.0) | 123.0, d | C5, C6, C14 | H6 |
| 8 | — | 140.0, s | — | — |
| 9 | 2.14, m | 47.3, d | C7, C8, C10 | H5, H11a, H12b, H15a |
| 10 | — | 38.5, s | — | — |
| 11a | 1.79, m | 21.8, t | C8, C9, C12, C13 | H1, H9, H11b |
| 11b | 1.48, dddd (12.6, 12.6, 12.6, 3.9) | | C9, C12 | H11a, H18, H19 |
| 12a | 1.65, ddd (13.7, 3.9, 3.9) | 39.5, t | C9, C11, C13, C14, C18 | H12b, H17, H18 |
| 12b | 1.59, ddd (13.7, 12.6, 3.0) | | C11, C13 | H9, H12a, H17 |
| 13 | — | 52.0, s | — | — |
| 14 | — | 84.7, s | — | — |
| 15a | 3.00, dd (16.0, 9.5) | 52.2, t | C8, C16 | H9, H15b, H16 |
| 15b | 2.01, dd (16.0, 2.9) | | C13, C14, C16, C17 | H15a |
| 16 | 4.90, ddd (9.5, 9.5, 2.9) | 60.3, d | C14, C22 | H15a, H17 |
| 17 | 3.12, d (9.5) | 58.9, d | C12, C13, C14, C15, C16, C23, C24 | H12a, H12b, H16, H18, H23 |
| 18 | 0.76, s | 17.6, q | C12, C13, C14, C17 | H11b, H12a, H17, H23, H24 |
| 19 | 1.05, s | 14.9, q | C1, C5, C9, C10 | H1, H6, H11b, H21 |
| 20 | 1.13, s | 25.5, q | C3, C4, C5, C21 | H5, H6 |
| 21 | 1.11, s | 22.5, q | C3, C4, C5, C20 | H6, H19 |
| 22 | — | 121.2, s | | |
| 23 | 7.46, d (2.3) | 152.4, d | C17, C22, C24, C26 | H17, H18 |
| 24 | 8.36, dd (9.8, 2.3) | 153.3, d | | H18, H25 |
| 25 | 6.22, d (9.8) | 112.8, d | C22, C26 | H24 |
| 26 | — | 164.6, s | — | — |

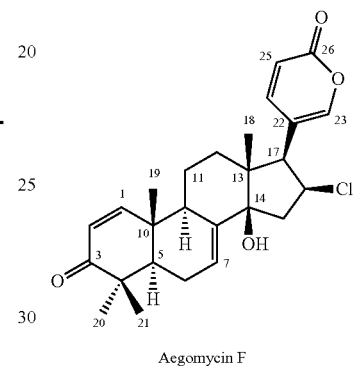

Aegomycin F

TABLE 7

$^1$H and $^{13}$C NMR data of Aegomycin G (CD$_3$OD).

| N° | $^1$H, m, J (Hz) | $^{13}$C, m | HMBC | ROESY |
|---|---|---|---|---|
| 1 | 5.81, br d (10.4) | 136.0, d | C3 | H2, H11a, H19 |
| 2 | 5.62, d (10.4) | 120.0, d | C4, C10 | H1, H3, OMe |
| 3 | 3.67, br s | 87.4, d | OMe, C1, C2, C4, C20, C21 | H2, H5, H20 |
| 4 | — | 37.7, s | — | — |
| 5 | 1.40, dd (12.0, 4.3) | 49.4, d | — | H3, H6a, H9, H20 |
| 6a | 2.07, m | 23.7, t | — | H5, H7, H20 |
| 6b | 1.99, m | | | H7, H21 |
| 7 | 6.08, br d (5.4) | 123.8, d | C14 | H6a, H6b |
| 8 | — | 140.6, s | — | — |
| 9 | 1.99, m | 49.0, d | — | H5, H15a |
| 10 | — | 38.6, s | — | — |
| 11a | 1.62, m | 21.8, t | — | H1, H11b |
| 11b | 1.45, dddd (12.6, 12.6, 12.6, 4.1) | | | H11a, H18, H19 |
| 12a | 1.58, m | 39.7, t | — | H17 |
| 12b | 1.54, m | | | H15a, H17 |
| 13 | — | 52.0, s | — | — |
| 14 | — | 85.0, s | — | — |
| 15a | 2.97, dd (15.7, 9.6) | 52.3, t | C17 | H9, H12b, H15b, H16 |
| 15b | 2.00, dd (15.7, 3.0) | | — | H15a |
| 16 | 4.89, ddd (9.6, 9.5, 3.0) | 60.3, d | — | H15a, H17 |
| 17 | 3.09, d (9.5) | 59.0, d | C12, C13, C14, C22, C24 | H12a, H12b, H16, H23 |
| 18 | 0.73, s | 17.6, q | C12, C13 C14,C17 | H11b, H24 |
| 19 | 0.90, s | 15.4, q | C1, C5, C9, C10 | H1, H11b |
| 20 | 0.97, s | 26.7, q | C4, C5, C3, C21 | H3, H5, H6a |
| 21 | 0.83, s | 17.2, q | C4, C5, C3, C20 | H6b |
| 22 | — | 121.3, s | | |
| 23 | 7.45, d (2.5) | 152.3, d* | C22, C24, C26 | H17 |

TABLE 7-continued

| | | $^1$H and $^{13}$C NMR data of Aegomycin G (CD$_3$OD). | | |
|---|---|---|---|---|
| N° | $^1$H, m, J (Hz) | $^{13}$C, m | HMBC | ROESY |
| 24 | 8.36, dd (9.9, 2.5) | 152.3, d* | — | H18, H25 |
| 25 | 6.21, d (9.9) | 112.7, d | C22, C26 | H24 |
| 26 | — | 164.7, s | — | — |
| OMe | 3.39, s | 58.3, q | C3 | H2 |

*Assignments may be interchanged

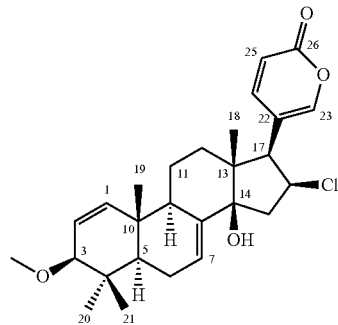

Aegomycin G

Example 4

Isolation of Aegomycin D, F and H

A third group of samples of the specimen of Example 1 (700 g) was triturated and extracted with H$_2$O and a mixture of MeOH:CH$_2$Cl$_2$ (50:50) at 23° C. The organic extract was evaporated under reduced pressure to yield a crude of 33 g. The crude was dissolved in MeOH:H$_2$O (1:9, 500 mL) and extracted with Hexane (3×500 mL), EtOAc (3×500 mL) and nBuOH (2×500 mL).

The Hexane fraction (4 g) was chromatographed (VLC) on Lichroprep RP-18 with a stepped gradient from H$_2$O:MeOH (3:1) to MeOH and then to CH$_2$Cl$_2$. The fraction eluted with H$_2$O:MeOH 1:3 (430 mg) was subjected to preparative reversed phase HPLC (Symmetry Prep C18, 19×150 mm, gradient H$_2$O:MeCN from 45 to 65% of MeCN in 30 min, UV detection, flow 14.6 mL/min) to yield 7 fractions (H1 to H7). Fraction H4 was subjected to semipreparative reversed phase HPLC(X Terra Phenyl, 10×150 mm, gradient H$_2$O:MeCN from 30 to 50% of MeCN in 30 min, UV detection, flow 3.8 mL/min) to yield Aegomycin F (8.3 mg). Fraction H5 was subjected to semipreparative reversed phase HPLC(X Terra Phenyl, 10×150 mm, gradient H$_2$O:MeCN from 45 to 60% of MeCN in 30 min, UV detection, flow 3.8 mL/min) to yield Aegomycin D (20.4 mg).

The EtOAc fraction (1.2 g) was chromatographed (VLC) on Lichroprep RP-18 with a stepped gradient from H$_2$O: MeOH (3:1) to MeOH and then to CH$_2$Cl$_2$. The fraction eluted with H$_2$O:MeOH 1:3 (162 mg) was subjected to preparative reversed phase HPLC (Symmetry Prep C18, 19×150 mm, gradient H$_2$O:MeCN from 45 to 65% of MeCN in 30 min, UV detection, flow 14.6 mL/min) to yield 7 fractions (H1 to H7). Fraction H2 was subjected to semipreparative reversed phase HPLC(X Terra Phenyl, 10×150 mm, gradient H$_2$O:MeCN from 30 to 55% of MeCN in 30 min, UV detection, flow 3.8 mL/min) to yield Aegomycin H (1.4 mg). Fraction H4 was subjected to semipreparative reversed phase HPLC(X Terra Phenyl, 10×150 mm, gradient H$_2$O:MeCN from 30 to 50% of MeCN in 20 min, UV detection, flow 3.8 mL/min) to yield Aegomycin F (12.2 mg). Fraction H5 was subjected to semipreparative reversed phase HPLC(X Terra Phenyl, 10×150 mm, gradient H$_2$O:MeCN from 45 to 60% of MeCN in 30 min, UV detection, flow 3.8 mL/min) to yield Aegomycin D (21.7 mg).

Aegomycin H: amorphous white solid. (+)ESIMS m/z 493 [M+H]$^+$, $^1$H (500 MHz) and $^{13}$C NMR (75 MHz) in CD$_3$OD see Table 8.

TABLE 8

| | | $^1$H and $^{13}$C NMR data of Aegomycin H (CD$_3$OD). | | |
|---|---|---|---|---|
| N° | $^1$H, m, J (Hz) | $^{13}$C, m | HMBC | ROESY |
| 1 | 7.10, d (10.3) | 156.7, d | C3, C4, C5, C9, C10, C19 | H2, H9, H11a, H19 |
| 2 | 5.91, d (10.3) | 126.4, d | C4, C10 | H1 |
| 3 | — | 206.5, s | — | — |
| 4 | — | 45.0, s | — | — |
| 5 | 1.89, dd (11.7, 4.5) | 48.5, d | C4, C6, C7, C9, C10, C19 | H9, H20 |
| 6 | 2.19, m | 24.0, t | C8 | H7, H19, H20, H21 |
| 7 | 6.15, m | 125.1, d | C5, C14 | H6 |
| 8 | — | 137.3, s | — | — |
| 9 | 2.27, m | 44.6, d | | H1, H5, H11a, H12, H15a |
| 10 | — | 38.6, s | — | — |
| 11a | 1.95, ddd (12.6, 4.2, 4.2) | 30.2, t | C8, C9, C12, C13 | H1, H9, H11b, H12 |
| 11b | 1.55, ddd (12.6, 12.6, 12.6) | | C8, C9, C10, C12, C13 | H11a, H18, H19 |
| 12 | 3.89, dd (12.6, 4.2) | 74.7, d | C17, C18 | H9, H11a, H15a, H17 |
| 13 | — | 58.2, s | — | |
| 14 | — | 84.9, s | — | |
| 15a | 3.33, d (15.9) | 63.7, t | C8, C14, C16 | H9, H12, H15b |
| 15b | 2.80, d (15.9) | | C13, C14, C16, C17 | H15a |
| 16 | — | 95.0, s | — | |
| 17 | 4.15, s | 68.2, d | C12, C13, C14, C16, C22, C23, C24 | H12, H18, H23 |
| 18 | 0.67, s | 10.4, q | C12, C13, C14, C17 | H11b, H17, H23, H24 |
| 19 | 1.07, s | 14.9, q | C1, C5, C9, C10 | H1, H6, H11b |
| 20 | 1.14, s | 25.4, q | C4, C5, C21 | H5, H6 |
| 21 | 1.12, s | 22.5, q | C4, C5, C20 | H6 |
| 22 | — | 119.9, s | — | |
| 23 | 7.55, d (2.6) | 153.0, d | C17, C22, C24, C26 | H17, H18 |
| 24 | 8.27, dd (9.8, 2.6) | 151.5, d | C23, C26 | H18, H25 |
| 25 | 6.28, d (9.8) | 113.7, d | C22, C26 | H24 |
| 26 | — | 164.1, s | — | |

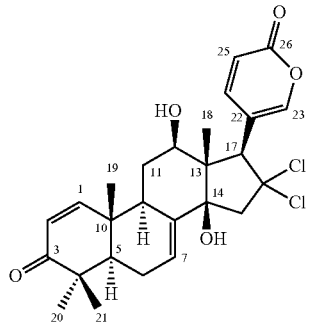

Aegomycin H

Example 5

Bioassays for the Detection of Antitumor Activity

The aim of this assay is to evaluate the in vitro cytostatic (ability to delay or arrest tumor cell growth) or cytotoxic (ability to kill tumor cells) activity of the samples being tested.

Cell Lines

| Name | N° ATCC | Species | Tissue | Characteristics |
|---|---|---|---|---|
| A549 | CCL-185 | human | lung | lung carcinoma (NSCLC) |
| HT29 | HTB-38 | human | colon | colorectal adenocarcinoma |
| MDA-MB-231 | HTB-26 | human | breast | breast adenocarcinoma |

Evaluation of Cytotoxic Activity Using the SBR Colorimetric Assay

A colorimetric assay, using sulforhodamine B (SRB) reaction has been adapted to provide a quantitative measurement of cell growth and viability (following the technique described by Skehan et al. J. Natl. Cancer Inst. 1990, 82, 1107-1112).

This form of assay employs SBS-standard 96-well cell culture microplates (Faircloth et al. Methods in Cell Science, 1988, 11(4), 201-205; Mosmann et al, Journal of Immunological Methods, 1983, 65(1-2), 55-63). All the cell lines used in this study were obtained from the American Type Culture Collection (ATCC) and derive from different types of human cancer.

Cells were maintained in Dulbecco's Modified Eagle Medium (DMEM) supplemented with 10% Fetal Bovine Serum (FBS), 2 mM L-glutamine, 100 U/mL penicillin and 100 U/mL streptomycin at 37° C., 5% $CO_2$ and 98% humidity. For the experiments, cells were harvested from subconfluent cultures using trypsinization and resuspended in fresh medium before counting and plating.

Cells were seeded in 96 well microtiter plates, at $5 \times 10^3$ cells per well in aliquots of 150 μL, and allowed to attach to the plate surface for 18 hours (overnight) in drug free medium. After that, one control (untreated) plate of each cell line was fixed (as described below) and used for time zero reference value. Culture plates were then treated with test compounds (50 μL aliquots of 4× stock solutions in complete culture medium plus 4% DMSO) using ten serial dilutions (concentrations ranging from 10 to 0.00262 μg/mL) and triplicate cultures (1% final concentration of DMSO). After 72 hours treatment, the antitumor effect was measured by using the SRB methodology: Briefly, cells were washed twice with PBS, fixed for 15 min in 1% glutaraldehyde solution at room temperature, rinsed twice in PBS, and stained in 0.4% SRB solution for 30 min at room temperature. Cells were then rinsed several times with 1% acetic acid solution and air-dried at room temperature. SRB was then extracted in 10 mM trizma base solution and the absorbance measured in an automated spectrophotometric plate reader at 490 nm. Effects on cell growth and survival were estimated by applying the NCI algorithm (Boyd M R and Paull K D. Drug Dev. Res. 1995, 34, 91-104).

Using the mean±SD of triplicate cultures, a dose-response curve was automatically generated using nonlinear regression analysis. Three reference parameters were calculated (NCI algorithm) by automatic interpolation: $GI_{50}$=compound concentration that produces 50% cell growth inhibition, as compared to control cultures; TGI=total cell growth inhibition (cytostatic effect), as compared to control cultures, and $LC_{50}$=compound concentration that produces 50% net cell killing (cytotoxic effect).

Tables 9 and 10 illustrate data on the biological activity of compounds of the present invention.

TABLE 9

Cytotoxicity assay-Activity Data (Molar) of Aegomycin A, B, C and D.

| | | Aegomycin A | Aegomycin B | Aegomycin C | Aegomycin D |
|---|---|---|---|---|---|
| MDA-MB-231 | $GI_{50}$ | 1.91E−8 | 7.61E−8 | 6.28E−8 | 6.48E−8 |
| | TGI | 3.63E−8 | 1.67E−7 | 1.97E−7 | 9.81E−8 |
| | $LC_{50}$ | 6.11E−8 | 3.81E−7 | 6.91E−7 | 1.73E−7 |
| HT29 | $GI_{50}$ | 1.05E−8 | 3.04E−8 | 9.84E−9 | 3.14E−8 |
| | TGI | 3.25E−8 | 2.28E−7 | 1.05E−7 | 1.35E−7 |
| | $LC_{50}$ | 1.15E−7 | 3.04E−6 | >2.09E−5 | 1.45E−6 |
| A549 | $GI_{50}$ | 3.82E−9 | 5.90E−9 | 7.54E−9 | 8.64E−9 |
| | TGI | 4.39E−9 | 7.61E−9 | 1.72E−8 | 1.28E−8 |
| | $LC_{50}$ | 5.35E−9 | 1.14E−8 | 4.19E−8 | 1.83E−8 |

TABLE 10

Cytotoxicity assay-Activity Data (Molar) of Aegomycin E, F, G and H

| | | Aegomycin E | Aegomycin F | Aegomycin G | Aegomycin F |
|---|---|---|---|---|---|
| MDA-MB-231 | $GI_{50}$ | 1.97E−7 | 8.80E−8 | 1.70E−7 | 8.11E−8 |
| | TGI | 3.65E−7 | 2.71E−7 | 4.36E−7 | 2.03E−7 |
| | $LC_{50}$ | 7.50E−7 | 9.48E−7 | 1.29E−6 | 6.08E−7 |
| HT29 | $GI_{50}$ | 1.18E−7 | 6.55E−8 | 1.46E−7 | 3.65E−8 |
| | TGI | 4.86E−7 | 4.06E−7 | 6.75E−7 | 2.03E−7 |
| | $LC_{50}$ | 5.27E−6 | 3.16E−6 | 3.92E−6 | 4.86E−6 |
| A549 | $GI_{50}$ | 4.26E−8 | 2.48E−8 | 3.92E−8 | 8.31E−9 |
| | TGI | 5.67E−8 | 3.84E−8 | 6.32E−8 | 1.46E−8 |
| | $LC_{50}$ | 7.50E−8 | 6.10E−8 | 1.11E−7 | 2.84E−8 |

The invention claimed is:

1. A purified compound of general formula I

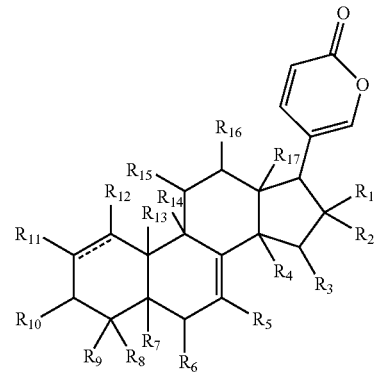

(I)

wherein each $R_1$ and $R_2$ is independently selected from hydrogen, halogen, $OR_a$, $OCOR_a$, and $OCOOR_a$, or $R_1$ and $R_2$ together are =O;

each $R_3$, $R_{15}$, and $R_{16}$ is independently selected from hydrogen, $OR_a$, $OCOR_a$, $OCOOR_a$, and =O, with the proviso that when a =O group exists the hydrogen of the C atom to which the =O is attached is absent;

each $R_4$, $R_5$, $R_6$, $R_7$, $R_{11}$, $R_{12}$, and $R_{14}$ is independently selected from hydrogen, $OR_a$, $OCOR_a$, and $OCOOR_a$;

each $R_8$, $R_9$, and $R_{17}$ is independently selected from hydrogen, $OR_a$, $OCOR_a$, $OCOOR_a$, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R_{10}$ is selected from hydrogen, $OR_b$, $OCOR_a$, $OCOOR_a$, and =O, with the proviso that when a =O group exists the hydrogen of the C atom to which the =O is attached is absent;

$R_{13}$ is selected from hydrogen, $COR_a$, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

each $R_a$ is independently selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group;

each $R_b$ is independently selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, substituted or unsubstituted heterocyclic group, and substituted or unsubstituted sugar; and the - - - - - - - line represents an additional bond, an epoxy group, or is absent;

or a pharmaceutically acceptable salt, prodrug or stereoisomer thereof.

2. A purified compound according to claim 1, wherein $R_3$, $R_5$, $R_6$, $R_{14}$, and $R_{15}$ are each independently selected from hydrogen, $OR_a$, and $OCOR_a$, and wherein $R_a$ is selected from hydrogen and substituted or unsubstituted $C_1$-$C_6$ alkyl.

3. A purified compound according to claim 2, wherein $R_3$, $R_5$, $R_6$, $R_{14}$, and $R_{15}$ are hydrogen.

4. A purified compound according to claim 1, wherein $R_{17}$ is a substituted or unsubstituted $C_1$-$C_6$ alkyl.

5. A purified compound according to claim 4, wherein $R_{17}$ is methyl.

6. A purified compound according to claim 1, having the following formula II

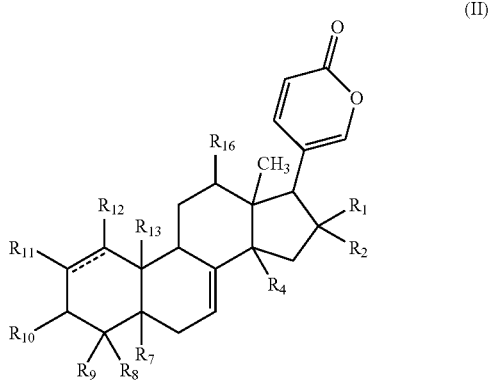

(II)

wherein $R_1$, $R_2$, $R_4$, $R_7$, $R_8$-$R_{13}$, $R_{16}$, and the - - - - - - - line are as defined in claim 1, or a pharmaceutically acceptable salt, prodrug or stereoisomer thereof.

7. A purified compound according to claim 1, wherein $R_1$ and $R_2$ are each independently selected from hydrogen, halogen, $OR_a$, and $OCOR_a$, and wherein $R_a$ is selected from hydrogen and substituted or unsubstituted $C_1$-$C_6$ alkyl.

8. A purified compound according to claim 7, wherein $R_1$ and $R_2$ are each independently selected from hydrogen and halogen.

9. A purified compound according to claim 1, wherein $R_4$ is selected from hydrogen and $OR_a$, and wherein $R_a$ is selected from hydrogen and substituted or unsubstituted $C_1$-$C_6$ alkyl.

10. A purified compound according to claim 9, wherein $R_4$ is —OH.

11. A purified compound according to claim 1, wherein $R_7$ is selected from hydrogen, $OR_a$, and $OCOR_a$, and wherein $R_a$ is selected from hydrogen and substituted or unsubstituted $C_1$-$C_6$ alkyl.

12. A purified compound according to claim 11, wherein $R_7$ is hydrogen.

13. A purified compound according to claim 1, wherein $R_8$ and $R_9$ are each independently selected from hydrogen, substituted or unsubstituted $C_1$-$C_{12}$ alkyl, $OR_a$, and $OCOR_a$, and wherein $R_a$ is selected from hydrogen and substituted or unsubstituted $C_1$-$C_6$ alkyl.

14. A purified compound according to claim 13, wherein $R_8$ and $R_9$ are substituted or unsubstituted $C_1$-$C_6$ alkyl.

15. A purified compound according to claim 1, wherein $R_{10}$ is selected from $OR_b$, $OCOR_a$, and =O, and wherein $R_a$ is selected from hydrogen and substituted or unsubstituted $C_1$-$C_6$ alkyl and $R_b$ is selected from hydrogen, substituted or unsubstituted $C_1$-$C_6$ alkyl, monosaccharide, disaccharide, and trisaccharide, with the proviso that when, $R_{10}$ is =O the hydrogen of the C atom to which $R_{10}$ is attached is absent.

16. A purified compound according to claim 15, wherein $R_{10}$ is =O or $OR_b$, wherein $R_b$ is methyl.

17. A purified compound according to claim 1, wherein $R_{13}$ is selected from hydrogen, substituted or unsubstituted $C_1$-$C_{12}$ alkyl, and $COR_a$, and wherein $R_a$ is selected from hydrogen and substituted or unsubstituted $C_1$-$C_6$ alkyl.

18. A purified compound according to claim 17, wherein $R_{13}$ is selected from substituted or unsubstituted methyl, substituted or unsubstituted ethyl, substituted or unsubstituted propyl, and COH.

19. A purified compound according to claim 1, wherein $R_{16}$ is selected from hydrogen, $OR_a$, and $OCOR_a$, and wherein $R_a$ is selected from hydrogen and substituted or unsubstituted $C_1$-$C_6$ alkyl.

20. A purified compound according to claim 19, wherein $R_{16}$ is hydrogen or OH.

21. A purified compound according to claim 1, wherein the - - - - - - - line is absent, $R_{11}$ and $R_{12}$ are each independently selected from hydrogen, $OR_a$, and $OCOR_a$, and $R_a$ is selected from hydrogen and substituted or unsubstituted $C_1$-$C_6$ alkyl.

22. A purified compound according to claim 1, wherein the line - - - - - - - represents an additional bond or an epoxy group, and $R_{11}$ and $R_{12}$ are hydrogen.

23. A purified compound according to claim 22, wherein an additional bond is present in the place indicated with the - - - - - - - line.

24. A purified compound according to claim 22, wherein an epoxy group is present in the place indicated with the - - - - - - - line.

25. A purified compound according to claim 1, having the following structure:

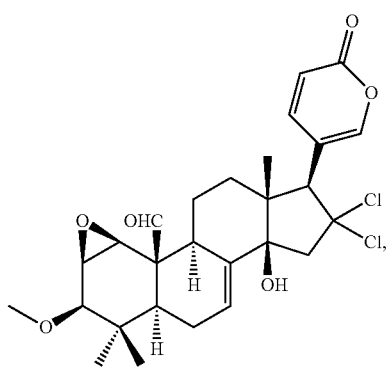
Aegomycin A
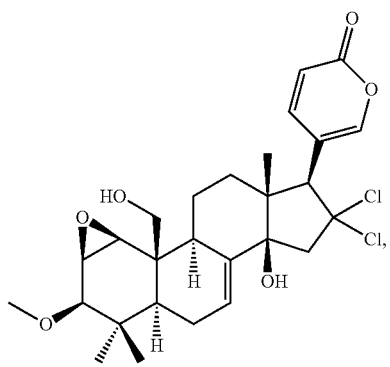
Aegomycin B
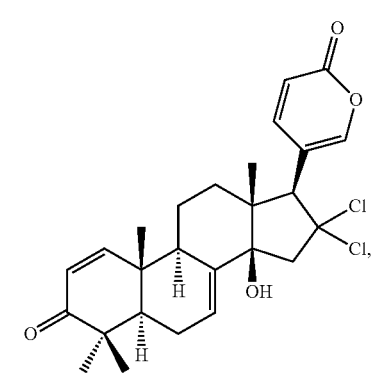
Aegomycin C
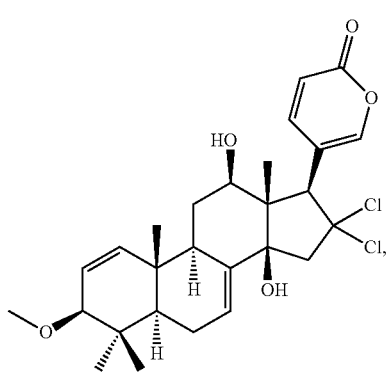
Aegomycin D
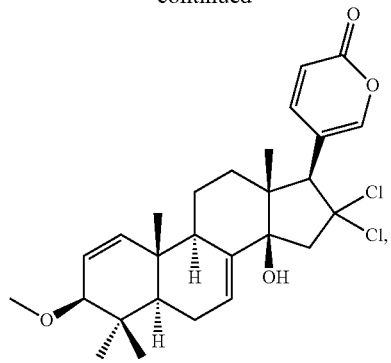
Aegomycin E
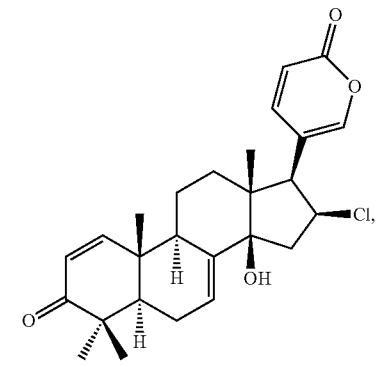
Aegomycin F
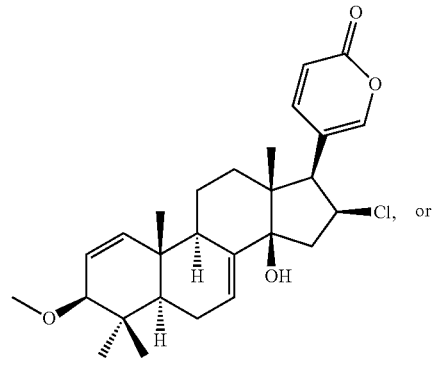
Aegomycin G
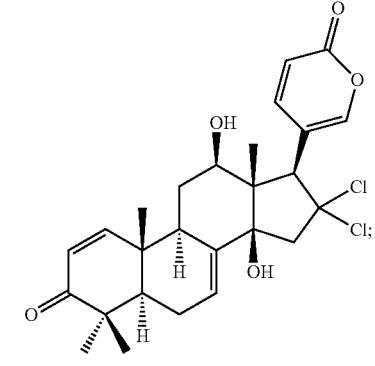
Aegomycin H
or a pharmaceutically acceptable salt, prodrug or stereoisomer thereof.
26. A pharmaceutical composition comprising a purified compound according to claim 1, or a pharmaceutically acceptable salt, prodrug or stereoisomer thereof, and a pharmaceutically acceptable carrier or diluent.

27. A method of treating a patient affected by cancer which comprises administering to said patient in need thereof, a therapeutically effective amount of a purified compound as defined in claim 1.

\* \* \* \* \*